(12) United States Patent
Washburn et al.

(10) Patent No.: US 6,500,122 B1
(45) Date of Patent: Dec. 31, 2002

(54) METHOD AND APPARATUS FOR REMOTELY POSITIONING REGION OF INTEREST IN IMAGE

(75) Inventors: Michael J. Washburn, New Berlin, WI (US); Patrick Robert Meyers, Mequon, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/473,002

(22) Filed: Dec. 28, 1999

Related U.S. Application Data

(63) Continuation-in-part of application No. 09/281,192, filed on Mar. 30, 1999, now Pat. No. 6,077,226.

(51) Int. Cl.$^7$ .............................................. A61B 8/00
(52) U.S. Cl. ...................................................... 600/443
(58) Field of Search ................................ 600/437–449, 600/454, 458, 450; 382/107, 110, 124, 130; 345/475

(56) References Cited

U.S. PATENT DOCUMENTS

| | | | |
|---|---|---|---|
| 5,997,478 A | * 12/1999 | Jackson et al. | ............. 600/437 |
| 6,077,226 A | * 6/2000 | Washburn et al. | ........... 600/443 |
| 6,126,605 A | * 10/2000 | Washburn et al. | ........... 600/454 |
| 6,149,597 A | * 11/2000 | Kamiyama | ................... 600/458 |

\* cited by examiner

*Primary Examiner*—Marvin M. Lateef
*Assistant Examiner*—Ali M. Imam
(74) *Attorney, Agent, or Firm*—Foley & Lardner; Peter J. Vogel; Michael A. Della Penna

(57) ABSTRACT

A method for displaying a region of interest graphic on an imaging system includes: (a) establishing a communication connection over a network between the imaging system and a remote facility; (b) displaying an image frame, the image frame having a reference point; (c) displaying a region of interest graphic on the image frame at a depth determined relative to the reference point, the region of interest graphic having a bottom width, a top width, a height, and an angle between a projection of a first edge line and a projection of a second edge line; (d) changing the depth of the region of interest; and (e) changing the top width and the angle of the region of interest graphic as a function of the change in depth, while maintaining the height and the bottom width of the region of interest graphic substantially unchanged. At least one of steps (b) through (e) is done remotely over the communication connection.

30 Claims, 11 Drawing Sheets

METHOD AND APPARATUS FOR REMOTELY POSITIONING REGION OF INTEREST IN IMAGE

CROSS-REFERENCE TO RELATED APPLICATIONS

This application is a continuation-in-part (CIP) of U.S. patent application Ser. No. 09/281,192, entitled "Method and Apparatus For Positioning Region Of Interest In Image" by Michael J. Washburn, et al., filed on Mar. 30, 1999, now U.S. Pat. No. 6,077,226.

BACKGROUND OF THE INVENTION

The present invention relates generally to the field of medical diagnostic systems, such as imaging systems. More particularly, the invention relates to an apparatus and technique for adjusting a region of interest relative to a sector-shaped background image frame in imaging systems.

Conventional ultrasound scanners create two-dimensional B-mode images of tissue in which the brightness of a pixel is based on the intensity of the echo return. Alternatively, in a color Doppler mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. Alternatively, in power Doppler imaging, the power contained in the returned Doppler signal is displayed.

Conventional ultrasound imaging systems comprise an array of ultrasonic transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. In the case of a steered array, by changing the time delays and amplitudes of the applied voltages, the beam with its focal point can be moved in a plane to scan the object. In the case of a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

A single scan line (or small localized group of scan lines) is acquired by transmitting focused ultrasound energy at a point, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

A B-mode ultrasound image is composed of multiple image scan lines. The brightness of a pixel is based on the intensity of the echo return from the biological tissue being scanned. The outputs of the receive beamformer channels are coherently summed to form a respective pixel intensity value for each sample volume in the object region or volume of interest. These pixel intensity values are log-compressed, scan-converted and then displayed as a B-mode image of the anatomy being scanned.

In addition, ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously laid over a B-mode image, each sample volume being color-coded to represent velocity of the moving material inside that sample volume at the time of interrogation.

Ultrasound scanners which perform color Doppler imaging employ an ROI (region of interest) which specifies the area of the gray-scale B-mode image to overlay with color Doppler data. The ROI is often made smaller than the B-mode image in order to maintain an acceptable acoustic frame rate. The scanner is programmed to allow the operator to move the ROI about the B-mode image area. In the case where a straight linear transducer is used, both the B-mode image area and the ROI are rectangles. Thus, as the depth of the ROI is changed, there is no need to automatically change the height or width of the ROI. However, in the cases where either a curved linear or a sector transducer is used, the scanner is programmed to automatically adjust the ROI size as the operator moves the ROI about the B-mode image area. In accordance with the conventional algorithm, the ROI is typically placed on or near the center of the B-mode image area. If the operator moves the ROI deeper in the image, the height of the ROI remains unchanged and the width of the ROI is changed automatically to accommodate the same number of vectors that were contained in the ROI at its previous position. Since the vectors are diverging with depth, the ROI width is increased as its depth increases. If instead the operator moves the ROI shallower in the image, the same algorithm is used, which results in a narrower ROI. Following the change in ROI position initiated by the operator and the automatic change in ROI width in response to that position change, the operator may then adjust the ROI width to restore the original ROI width. This latter adjustment is desirable in the case where the depth of the ROI is increased because the resulting acoustic frame rate will be increased. This conventional method of operating an ultrasound scanner has the disadvantage that an additional adjustment must be made by the operator following increase in ROI depth in order to gain the benefit of increased acoustic frame rate.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems discussed above. In particular, there is a need for adjusting a region of interest remotely over a network. Further, there is a need for a variety of remote services in imaging systems, such as, remote control, software upgrades, diagnostics, servicing, and resource pooling.

SUMMARY OF THE INVENTION

One embodiment of the invention relates to a method for displaying a region of interest graphic on an imaging system including: (a) establishing a communication connection over a network between the imaging system and a remote facility; (b) displaying an image frame, the image frame having a reference point; (c) displaying a region of interest graphic on the image frame at a depth determined relative to the reference point, the region of interest graphic having a bottom width, a top width, a height, and an angle between a projection of a first edge line and a projection of a second edge line; (d) changing the depth of the region of interest; and (e) changing the top width and the angle of the region of interest graphic as a function of the change in depth, while maintaining the height and the bottom width of the region of interest graphic substantially unchanged. At least one of steps (b) through (e) is done remotely over the communication connection.

Another embodiment of the invention relates to an imaging method for an imaging system including: (a) establishing a communication connection over a network between an imaging system and a remote facility; (b) acquiring first imaging data in a first imaging mode from a first region in a scan plane; (c) acquiring second imaging data in a second imaging mode from a second region in the scan plane; (d) displaying the first imaging data in a region of interest of an image frame having a reference point, the region of interest being in the shape of a sector of an annular ring and placed at a depth determined relative to the reference point; (e) displaying the second imaging data in a portion of the image frame lying outside the region of interest; (f) changing the depth of the region of interest; (g) adjusting the shape of the region of interest by changing a top width of the region of interest as a function of the change in depth while maintaining a height and a bottom width of the region of interest substantially constant; (h) acquiring third imaging data in the first imaging mode from a third region in the scan plane; (i) acquiring fourth imaging data in the second imaging mode from a fourth region in the scan plane; (j) displaying the third imaging data in the adjusted region of interest; and (k) displaying the fourth imaging data in a portion of the image frame lying outside the adjusted region of interest. At least one of steps (b) through (k) is done remotely over the communication connection.

Another embodiment of the invention relates to an imaging system including: (a) means for establishing a communication connection over a network between the imaging system and a remote facility to provide remote services to the imaging system; (b) a display subsystem; (c) means for controlling the display subsystem to display an image frame, the image frame having a reference point; (d) means for controlling the display subsystem to display a region of interest graphic on the image frame at a depth determined relative to the reference point, the region of interest graphic having a bottom width, a top width, a height, and an angle between a projection of a first edge line and a projection of a second edge line; (e) means for changing the depth of the region of interest; and (f) means for changing the top width and the angle of the region of interest graphic as a function of the change in depth, while maintaining the height and the bottom width of the region of interest graphic substantially unchanged.

Another embodiment of the invention relates to an imaging system including: (a) means for establishing a communication connection over a network between an imaging system and a remote facility to provide remote services to the imaging system; (b) a display subsystem; (c) means for acquiring first imaging data in a first imaging mode from a first region in a scan plane; (d) means for acquiring second imaging data in a second imaging mode from a second region in the scan plane; (e) means for controlling the display subsystem to display the first imaging data in a region of interest of an image frame having a reference point, the region of interest being in the shape of a sector of an annular ring and placed at a depth determined relative to the reference point; (f) means for controlling the display subsystem to display the second imaging data in a portion of the image frame lying outside the region of interest; (g) means for changing the depth of the region of interest; (h) means for adjusting the shape of the region of interest by changing a top width of the region of interest as a function of the change in depth, while maintaining a height and a bottom width of the region of interest substantially constant; (i) means for acquiring third imaging data in the first imaging mode from a third region in the scan plane; (j) means for acquiring fourth imaging data in the second imaging mode from a fourth region in the scan plane; (k) means for controlling the display subsystem to display the third imaging data in the adjusted region of interest; and (l) means for controlling the display subsystem to display the fourth imaging data in a portion of the image frame lying outside the adjusted region of interest. At least one of the means (b) through (l) is located remotely.

Another embodiment of the invention relates to an imaging system including: a display subsystem and a network operatively coupled to the display subsystem. The network provides for the following steps, at least one of which is done remote from the display subsystem: controlling the display subsystem to display an image frame, the image frame having a reference point; controlling the display subsystem to display a region of interest graphic on the image frame at a depth determined relative to the reference point, the region of interest graphic having a bottom width, a top width, a height, and an angle between a projection of a first edge line and a projection of a second edge line; changing the depth of the region of interest; and changing the top width and the angle of the region of interest graphic as a function of the change in depth while maintaining the height and the bottom width of the region of interest graphic substantially unchanged.

Other principle features vantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements, and.

DETAILED DESCRIPTION OF THE PREFERRED EMBODIMENT

Figure 1:
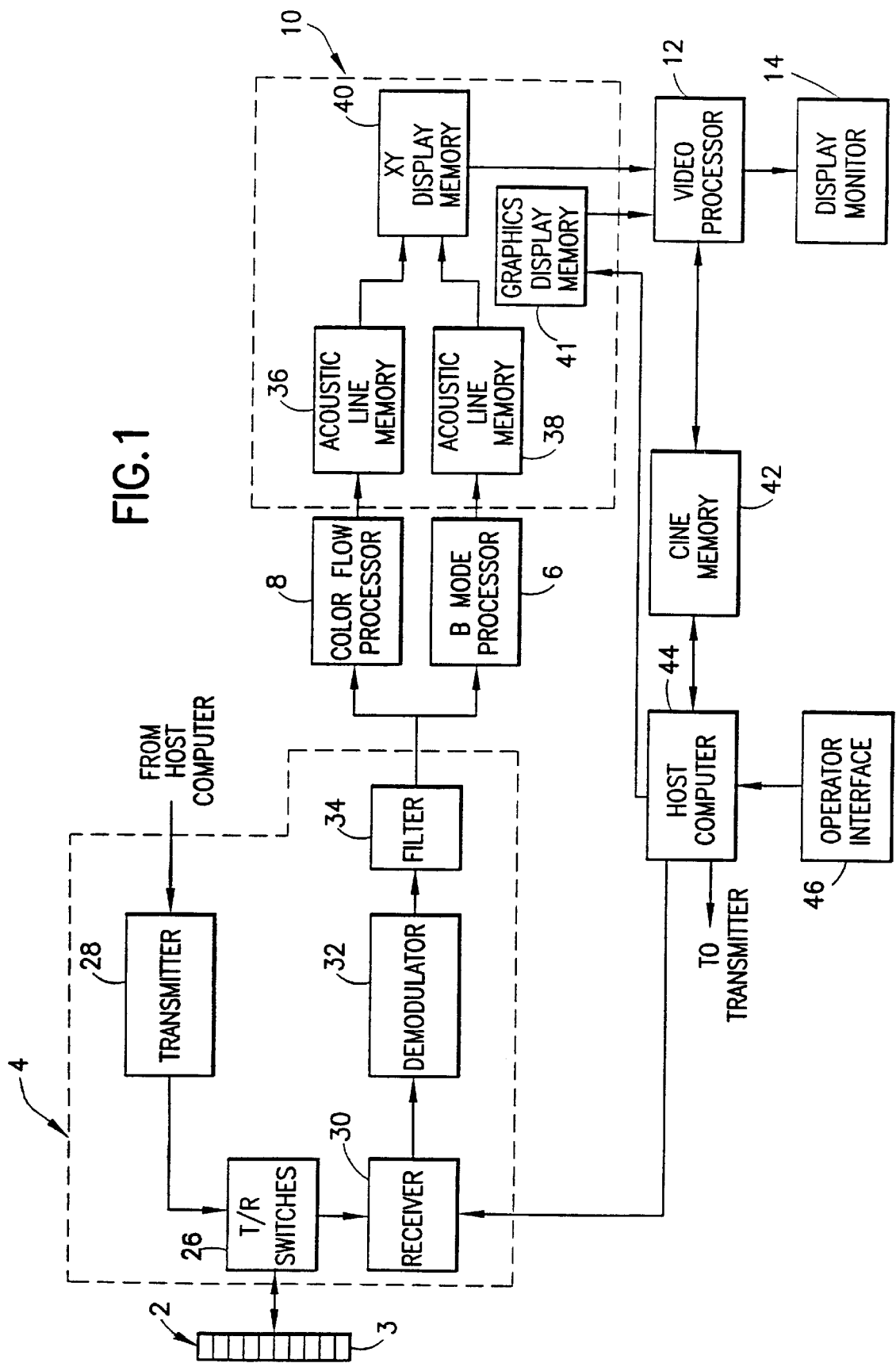
FIG. 1 is a block diagram showing the B mode and color flow mode signal processing chains for one type of ultrasound imaging system in which the present invention can be incorporated.

Referring to FIG. 1, the ultrasound imaging system comprises a transducer array 2 consisting of a plurality of separately driven transducer elements 3. The transducer is connected to a beamformer 4 comprising a transmitter 28 and a receiver 30. In a transmit mode, a set of transmit/receive (T/R) switches 26 couple the transducer elements to transmitter 28. Each transducer element 3 produces a burst of ultrasonic energy when energized by a respective pulsed waveform produced by transmitter 28. In a receive mode, the T/R switches 26 couple the transducer elements to receiver 30. The ultrasonic energy reflected back to transducer array 2 from the object under study is converted to an analog electrical signal by each receiving transducer element 3 and applied separately to receiver 30. The transmitter and receiver are operated under control of a host computer (i.e., master controller) 44. A complete scan is performed by acquiring a series of echoes in which transmitter 28 is gated ON momentarily to energize each transducer element 3 in the transmit aperture, and the subsequent echo signals produced by each transducer element are applied to receiver 30. The receiver 30 converts the analog echo signals to digital signals and combines the respective digital signals derived from each transducer element to produce a single beam-summed signal which is used to produce a line in an image displayed by a display monitor 14.

Figure 3:
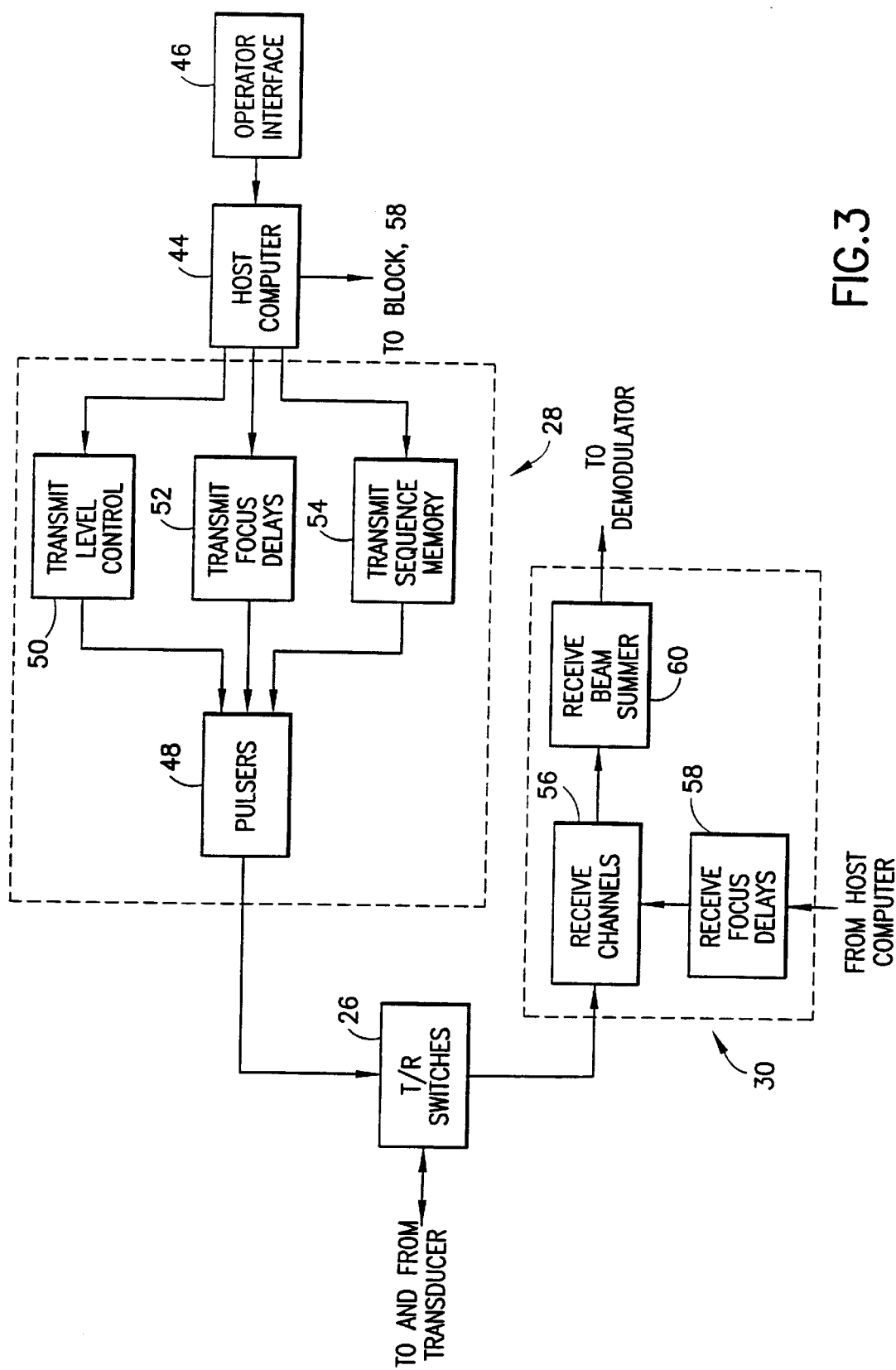
FIG. 3 is a block diagram showing the transmitter and receiver of FIG. 2 in greater detail.

Referring to FIG. 3, each transducer element in a transmit aperture is pulsed by a pulse waveform output by a respective pulser 48 in response to a respective transmit sequence output to that pulser from a transmit sequence memory 34. Adjustment of the transmit waveform frequency and/or length is implemented by programming transmit sequence memory 34. The frequency and length of each pulse waveform is determined by the respective transmit sequence. For example, if the pulsers 48 are bipolar, +1 and −1 elements of a transmit sequence are transformed into pulses of opposite phase by each pulser, while 0 elements correspond to no pulse. The duty cycle or pulse width is proportional to the number of consecutive +1's or −1's in the transmit sequence.

Under the direction of the host computer 44, the transmitter 28 drives the transducer array 2 such that the ultrasonic energy is transmitted as a directed focused beam. To accomplish focusing, respective time delays are imparted to the pulsers 48 by a transmit focus delay block 52, while respective pulse amplitudes are set by transmit level control block 50. The pulsers send the transmit pulses to elements of the transducer array 2 via the T/R switches 26. By appropriately adjusting the transmit focus time delays in a conventional manner, an ultrasonic beam can be directed and focused at a transmit focal zone position. The axial length of the transmit focal zone is a function of the width of the transmit aperture.

The host computer 44 determines the conditions under which the acoustic pulses will be transmitted. With this information, the transmit focus delay and transmit level control blocks will respectively determine the timing and the amplitude of each of the transmit pulses to be generated by the pulsers 48, while the frequency and length of the transmit pulses are determined by the transmit sequences. The host computer can provide different sets of transmit sequences, transmit focus delays and transmit levels for B-mode and color flow mode imaging.

After each transmit, the T/R switches 26 are switched to receive mode to accept the returning echoes backscattered from the object being scanned. These return signals are fed to respective receive channels 56 of the receiver 30. Each receive channels includes an analog-to-digital converter. The receiver tracks echoes under the direction of the host computer 44 by imparting the proper receive focus time delays 58 to the received RF echo signals. The beam summer 60 sums the RF echo signals for each firing to provide an echo signal which accurately indicates the total ultrasonic energy reflected from a succession of ranges corresponding to the particular transmit focal position.

Referring again to FIG. 1, in baseband imaging systems the beamsummed signal is output to a demodulator 32, which converts the beamsummed signal into baseband in-phase I and quadrature Q data Vectors. The I and Q acoustic data vectors from the demodulator 32 are output to an FIR filter 34, which is provided with filter coefficients from a filter coefficient memory (not shown). The filter coefficient memory is programmed by the host computer 44.

The acoustic data from filter 34 is sent to a switch (not shown). In the B mode, acoustic data vectors acquired during scanning of an entire image frame are output to the B-mode processor 6. In the color flow mode, acoustic data vectors acquired during scanning of an ROI are output to a color flow processor 8. Depending on whether the acoustic data is for the background image or the ROI, the output of filter 34 is channeled to the appropriate processor.

Figure 2:
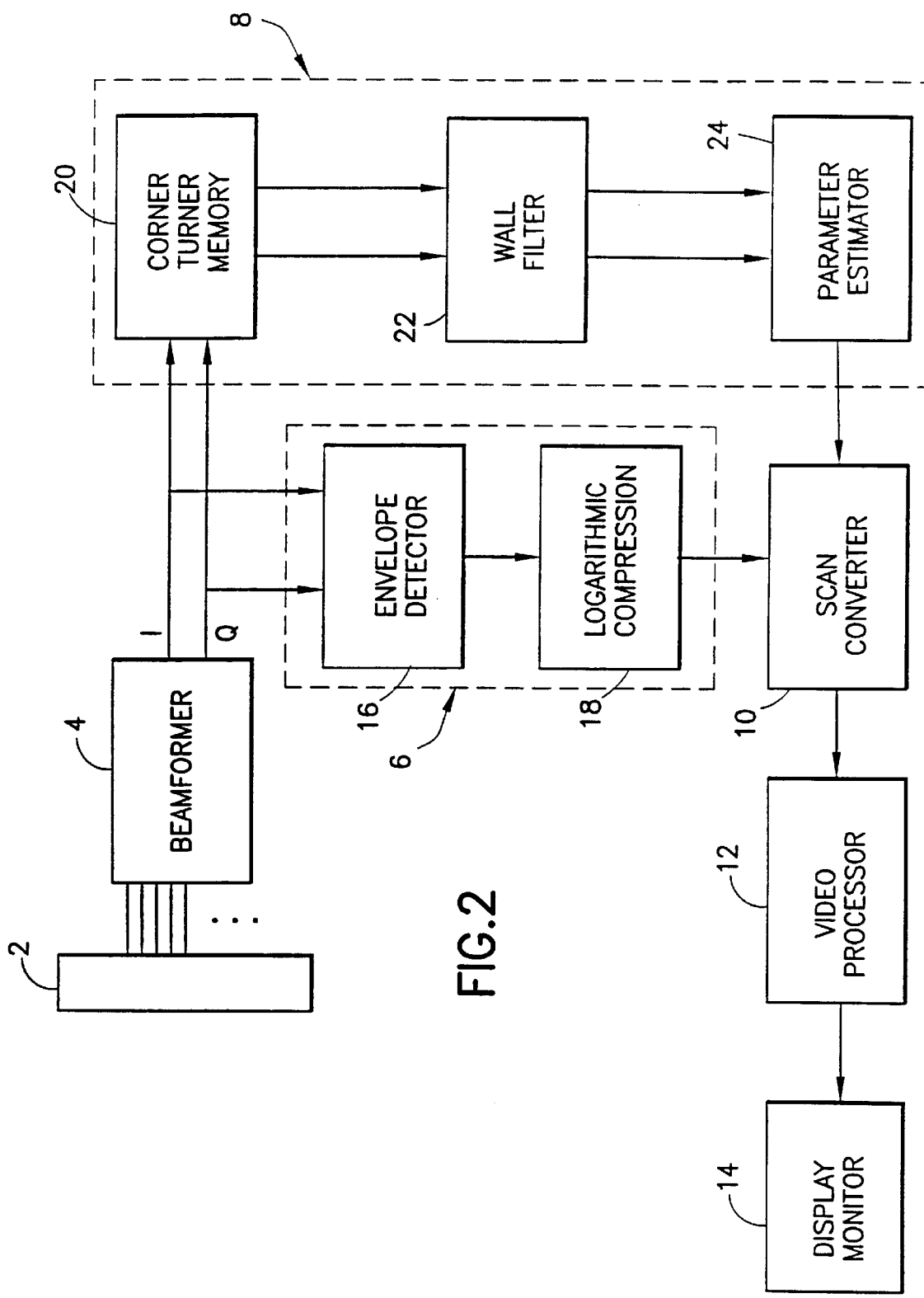
FIG. 2 is a block diagram showing additional components of the system depicted in FIG. 1.

In the B mode, the B-mode processor 6 detects the envelope of the streams of I and Q acoustic data (envelope detector 16 in FIG. 2) and then log-compresses the respective signal envelopes (logarithmic compression block 18 in FIG. 2). The envelope of a baseband signal is the magnitude of the vector which I and Q represent. The I,Q phase angle is not used in the B-mode display. The magnitude (i.e., intensity) of the signal is the square root of the sum of the squares of the orthogonal components, i.e., $(I^2+Q^2)^{1/2}$.

Referring again to FIG. 1, the B-mode intensity data is output to a B-mode acoustic line memory 38 in the scan converter 12. The acoustic line memory 38 accepts the processed vectors of B-mode intensity data acquired during scanning of the background area and interpolates where necessary. The acoustic line memory 38 also performs the coordinate transformation of the B-mode intensity data from polar coordinate (R-θ) sector format or Cartesian coordinate linear format to appropriately scaled Cartesian coordinate display pixel intensity data. The pixel intensity data for background image area is written into an X-Y display memory 40.

The scan-converted B-mode image frame stored in the X-Y display memory 40 is passed to a video processor 12, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 14 for display.

Before gray mapping, successive frames of display pixel intensity data in the video processor 12 are stored in a cine memory 42 on a first-in, first-out basis. Storage can be continuous or as a result of an external trigger event. The cine memory 42 is like a circular image buffer that runs in the background, capturing image data that is displayed in real time to the user. When the user freezes the system (by operation of an appropriate device on the operator interface 46), the user has the capability to view image data previously captured in cine memory.

System control is centered in host computer 44, which accepts operator inputs through the operator interface 46 (e.g., a control panel) and in turn controls the various subsystems. The host computer 44 performs system level control functions. A system control bus (not shown) provides the interface from the host computer to the subsystems. The host computer preferably incorporates a scan controller (not shown) which provides real-time (acoustic vector rate) control inputs to the various subsystems. The scan controller is programmed by the host computer CPU with the vector sequences and synchronization options for acoustic frame acquisitions. Thus, the scan controller controls the beam distribution and the beam density. The scan controller transmits the beam parameters defined by the host computer CPU to the subsystems via a scan control bus (not shown). Alternatively, the scan controller can be a separate dedicated processor programmed by the host computer.

The B-mode images displayed by monitor 14 are produced from an image frame of data in which each datum indicates the intensity or brightness of a respective pixel in the display. An image frame may, e.g., comprise a 256×256 data array in which each display pixel intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a scan plane through the body being imaged.

In the color flow mode, the color flow processor 8 converts the streams of I and Q acoustic data into color flow estimates of velocity or power. Given the angle θ between the insonifying beam and the flow axis, the magnitude of the velocity vector can be determined by the standard Doppler equation:

$$v = cf_d/(2f_0 \cos \theta) \tag{1}$$

where c is the speed of sound in blood, $f_0$ is the transmit frequency and $f_d$ is the motion-induced Doppler frequency shift in the backscattered ultrasound.

In one conventional ultrasound imaging system, the ultrasound transducer array 2 is activated to transmit a series of multi-cycle (typically 4–8 cycles) waveforms which are focused at the same transmit focal position with the same transmit characteristics. These waveforms are fired at a pulse repetition frequency (PRF). A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by receiver 30. This process is repeated for multiple points in an ROI selected by the system operator via an operator interface 46.

The traditional color firing sequence is a series of firings focused at the same transmit focal position, which firings produce the respective receive signals:

$$F_1\ F_2\ F_3\ F_4\ \ldots\ F_M$$

where $F_i$ is the receive signal for the i-th firing and M is the number of firings in a packet. These receive signals are then sent to the color flow processor 8. Referring to FIG. 2, a typical color flow processor 8 comprises a corner turner memory 20, respective wall filters 22 for the I/Q components, and a parameter estimator 24. The I/Q components are loaded into the corner turner memory 20, whose purpose is to buffer data from possibly interleaved firings and output the data as vectors of points across firings at a given range cell. Data is received in "fast time", or sequentially down range (along a vector) for each firing. The resultant "slow time" I/Q signal samples are passed through respective wall filters 22. In a typical system, each wall filter is a high pass filter which is applied to each down range position across firings, i.e., in "slow time". In the simplest case of a (1, −1) wall filter, each range point will be filtered to produce the respective difference signals:

$$(F_1-F_2)\ (F_2-F_3)\ (F_3-F_4)\ \ldots\ (F_{M-1}-F_M)$$

and these differences are input to the color flow parameter estimator 24.

The purpose of the wall filter is to remove signal components produced by tissue surrounding the blood flow of interest. If these signal components are not removed, the resulting velocity estimate will be a combination of the velocities from the blood flow and the surrounding tissue. The backscatter component from tissue is many times larger than that from blood, so the velocity estimate will most likely be more representative of the tissue, rather than the blood flow. In order to get the flow velocity, the tissue signal must be filtered out.

The wall-filtered outputs are fed into the parameter estimator 24, which converts the range cell information into the intermediate autocorrelation parameters N, D, and R(0). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the input data for firing i, and M is the number of firings in the packet. R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (4)$$

R(0) indicates the power in the returned ultrasound echoes.

A processor in parameter estimator 24 converts N and D into a magnitude and phase for each range cell. The equations used are as follows:

$$|R(T)| = \sqrt{N^2 + D^2} \quad (5)$$

$$\Phi(R(T)) = \tan^{-1}\left[\frac{N}{D}\right] \quad (6)$$

The parameter estimator 24 processes the magnitude and phase values into estimates of power, velocity and turbulence. The phase is used to calculate the mean Doppler frequency, which is proportional to the velocity as shown below; R(0) and |R(T)| (magnitude) are used to estimate the turbulence.

The mean Doppler frequency is obtained from the phase of N and D and the pulse repetition time T:

$$\bar{f} = \frac{1}{2\pi T}\tan^{-1}\left[\frac{N}{D}\right] = \frac{1}{2\pi T}(\Phi(R(T))) \quad (7)$$

The mean velocity is calculated using the Doppler shift equation:

$$\bar{v} = \frac{\bar{f}}{f_0} \frac{c}{2\cos\theta} \quad (8)$$

The parameter estimator 24 does not calculate the mean Doppler frequency as an intermediate output, but calculates directly from the phase output of a processor using a lookup table. Typically the power estimates are compressed before scan conversion, e.g., using logarithmic compression (not shown).

The color flow estimates (i.e., power or velocity) are sent to a color flow acoustic line memory 36 of scan converter 14, which converts the color images into X-Y format for video display and stores the converted image in the X-Y display memory 40. The scan-converted color images are then passed to the video processor 12, which maps the video data to a display color map for video display. The color flow image data is then sent to the video monitor 14 for display in an ROI superimposed on the B-mode image data.

Figure 4:
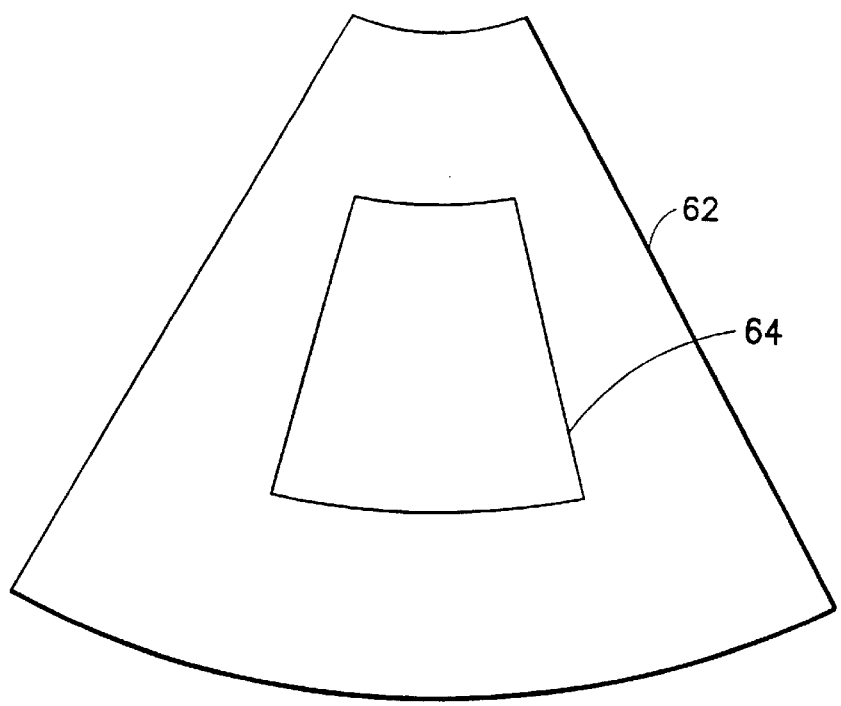
FIG. 4 is a schematic depicting a sector scan in which an ROI image is superimposed on a background image area at a default position in accordance with a conventional technique.

Referring to FIG. 4, during display an ROI graphic 64 is superimposed on the B-mode image area 62. Within the perimeter of that ROI graphic, color flow data is superimposed on the B-mode data. FIG. 4 shows the default position for the ROI graphic. The display data representing the ROI graphic 64 in the default position is generated by the host computer 44 and stored in a graphics display memory 41 of the scan converter 10. Alternatively, the graphics data can be generated by a dedicated graphics processor which communicates with the host computer. The ROI graphic data is output from graphics display memory 41 to the video processor 12 for continuous display, i.e., as the color flow and B-mode data for each successive image frame are displayed, an unchanging ROI is displayed to demarcate the boundary of the color flow data. superimposed on the B-mode data.

In accordance with the preferred embodiment of the present invention, the width and height of the ROI can be adjusted by manipulation of respective control knobs on the operator interface 46. The position of the ROI can be changed by manipulation of a third control knob. Alternatively, the position and size of the ROI can be adjusted via any other standard user interface device (e.g., a trackball).

Depending on the dimensions and position of the ROI, in the color flow mode the host computer 44 will provide the required beam parameters to the transmitter 28 and to the receiver 30. The ROI imaging parameters, including transmit waveforms, number of transmit focal zones, vector spacing, filter coefficients and frame rates are all independent of those for the background B-mode image.

Figure 5:
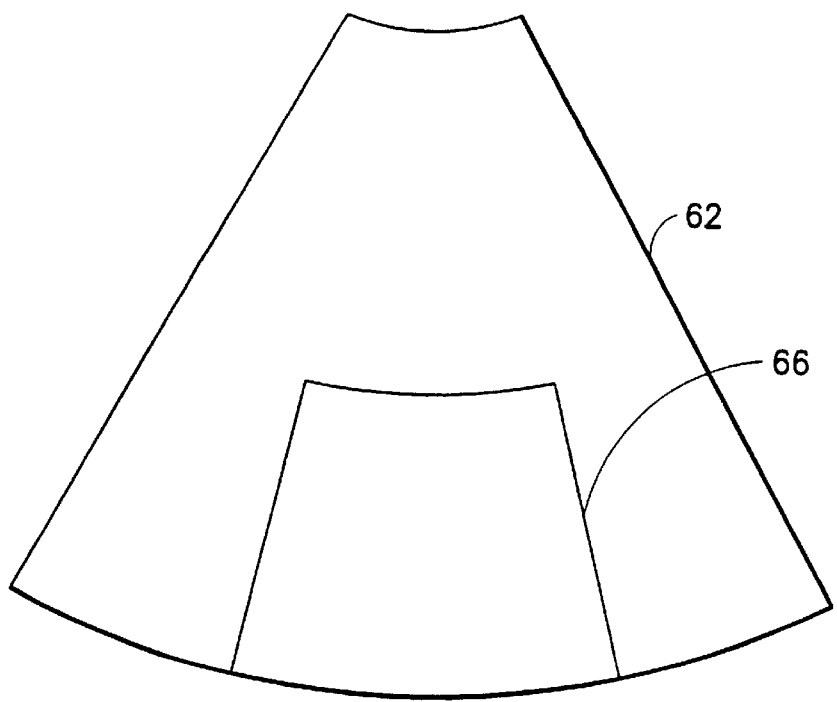
FIG. 5 is a schematic depicting a sector scan in which the ROI image of FIG. 4 has been moved to the bottom of the background image area and adjusted in accordance with a conventional algorithm.
Figure 6:
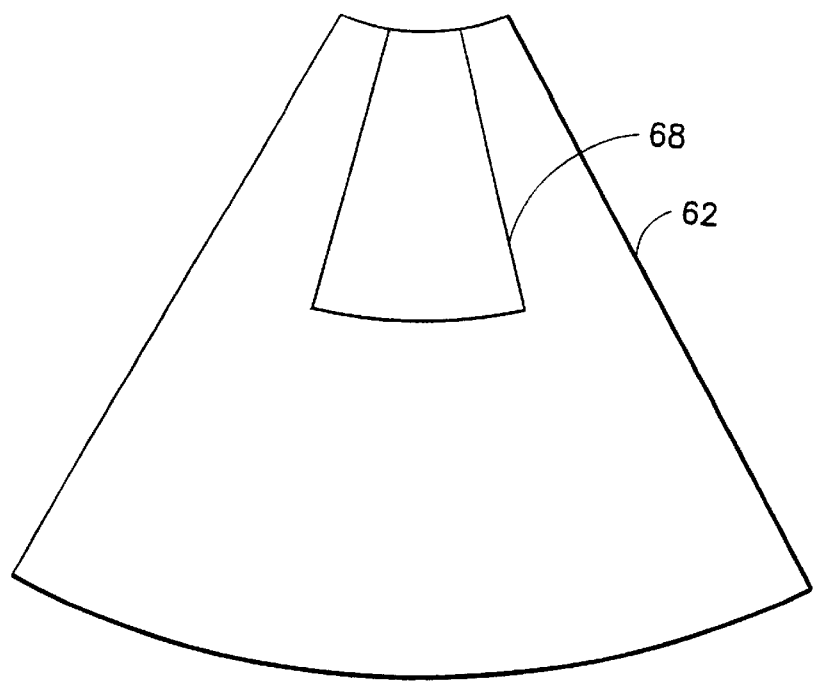
FIG. 6 is a schematic depicting a sector scan in which the ROI image of FIG. 4 has been moved to the top of the background image area and adjusted in accordance with the conventional algorithm.

In a conventional system, the default position of the ROI 64 is typically on or near the center of the B-mode image area 62, as depicted in FIG. 4. In accordance with a known algorithm, as the ROI is moved by the operator, the system automatically reconfigures the ROI to maintain a constant number of vectors therein. If the operator moves the ROI deeper in the image, the height of the ROI remains unchanged and the width of the ROI is changed automatically to accommodate the same number of vectors that were contained in the ROI at its previous position, thereby maintaining the acoustic frame rate constant. Such a deeper ROI is designated by numeral 66 in FIG. 5. Since the vectors are diverging with depth, the width of ROI 66 in FIG. 5 is greater than the width of the ROI 64 in FIG. 4. If the operator moves the ROI shallower in the image, the same algorithm produces a narrower ROI. Such a narrower ROI is designated by numeral 68 in FIG. 6. Following a change in ROI position initiated by the operator and the automatic change in ROI width in response to that position change, the operator may then adjust the ROI width to restore the original ROI width.

Figure 7:
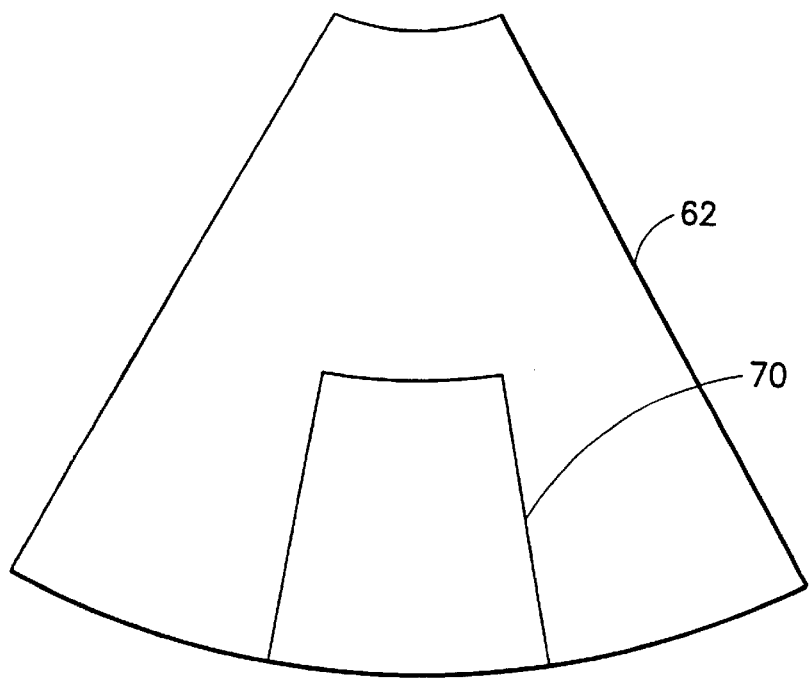
FIG. 7 is a schematic depicting a sector scan in which the ROI image of FIG. 4 has been moved to the bottom of the background image area and adjusted in accordance with the algorithm of the preferred embodiment.
Figure 8:
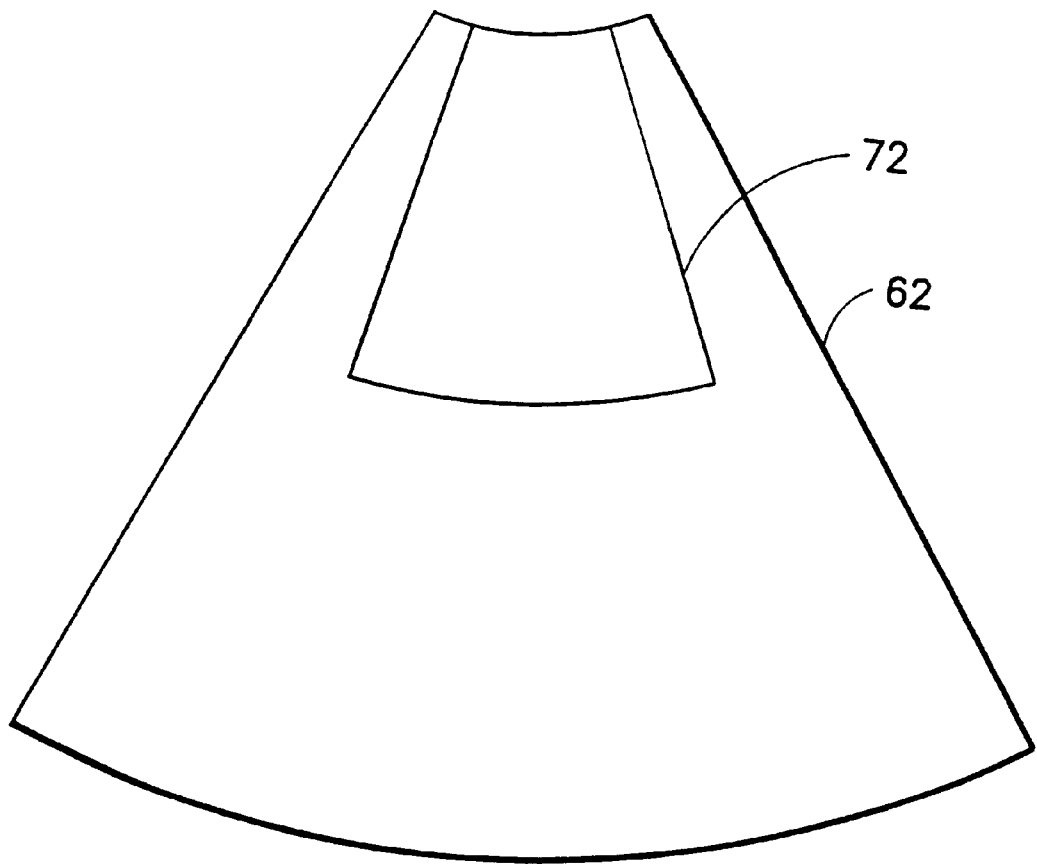
FIG. 8 is a schematic depicting a sector scan in which the ROI image of FIG. 4 has been moved to the top of the background image area and adjusted in accordance with the algorithm of the preferred embodiment.

In contrast to the foregoing conventional algorithm, the algorithm employed in the present invention does not seek to maintain a constant number of vectors in an ROI during position changes. Instead the algorithm in accordance with the preferred embodiment maintains the height and the bottom width of the ROI constant during operator-initiated changes in the ROI position. Only the top width of the ROI is automatically changed in response to the position change. For example if the user moves the ROI deeper in the image (e.g., from the default position shown in FIG. 4 to the position shown in FIG. 7), the height and the width of the bottom of the ROI are not changed, i.e., the height and bottom width of ROI 70 in FIG. 7 will be the same as the height and bottom width respectively of ROI 64 in FIG. 4. The width at the top of the ROI 70, however, is increased and the angles of the edges of the ROI 70 are changed such that the ROI edges are respectively parallel to the leftmost and rightmost vectors of color flow data within the bottom region of ROI 70. If instead, the user moves the ROI shallower in the image, the height of the ROI and the width of the bottom of the ROI are again unchanged. As seen in FIG. 8, the width at the top of the ROI 72 is decreased relative to the top width of ROI 64 in FIG. 4 and the angles of the edges of the ROI 72 are again changed such that the ROI edges are respectively parallel to the leftmost and rightmost vectors of color flow data within the bottom region of ROI 70.

In accordance with one preferred embodiment, the first imaging mode is the B mode and the second imaging mode is the color Doppler mode. In another preferred embodiment, the first imaging mode is the B mode and the second imaging mode is a zoom B mode. In yet another preferred embodiment, the first imaging mode is a non-optimal image quality B mode and the second imaging mode is an optimal image quality B mode.

In each preferred embodiment, the shape of the ROI is automatically adjusted in response to a change in ROI depth. Both the ROI and the image frame on which the ROI is placed are in the shape of a sector of an annular ring, i.e., a top arc and a bottom arc connected at their respective ends by left and right edge lines, the arcs of both the ROI and the image frame having a common center of curvature at which the projections of the edge lines intersect. This common center of curvature is referred to herein as the "apex of the image frame". In accordance with the preferred embodiments, the height and width of the ROI are not changed as the depth of the ROI is changed. The height is the distance from the midpoint of the bottom arc of the ROI to the midpoint of the top arc, while the width is the distance from the midpoint of the bottom arc of the ROI to the point at which the projection of one edge line of the ROI intersects a line tangent to the midpoint of the bottom arc. The host computer or a dedicated graphics processor (not shown) computes the angle included between the midline from the apex of the image frame to the midpoint of the bottom arc and a line projecting from an edge line to the apex of the image frame. Based on that angle, the half-width and the distance of the bottom arc midpoint to the image frame apex, the computer or graphics processor determines the coordinates of those pixels on the display monitor which are to be filled with graphics data representing one edge line of the ROI. A similar computation is done to determine the coordinates of those pixels on the display monitor which are to be filled with graphics data representing the other edge line of the ROI. Also the coordinates of those pixels on the display monitor which are to be filled with graphics data representing the top and bottom arcs of the ROI are determined. The computer or graphics processor then inputs the data representing the ROI graphic into a graphic display memory at the addresses corresponding to the determined pixel coordinates.

In the preferred embodiment in which color flow data is to be superimposed in an ROI on an image frame of B-mode data, after the boundaries of a new ROI have been determined in response to an operator-actuated change in ROI depth, the host computer 44 (see FIG. 1) transmits new beam parameters to the transmit and receive beamformers 28 and 30 for use in the color flow mode. These beam parameters limit the acquisition of color flow data to a region in the scan plane substantially corresponding to the ROI on the image frame. The same principle of operation applies in the other preferred embodiments, to wit, the system computer broadcasts a first set of beam parameters for acquiring data in a region of the scan plane in the first imaging mode and broadcasts a second set of beam parameters for acquiring data in only that portion of the region of the scan plane corresponding to the ROI in the second imaging mode.

Figure 10:
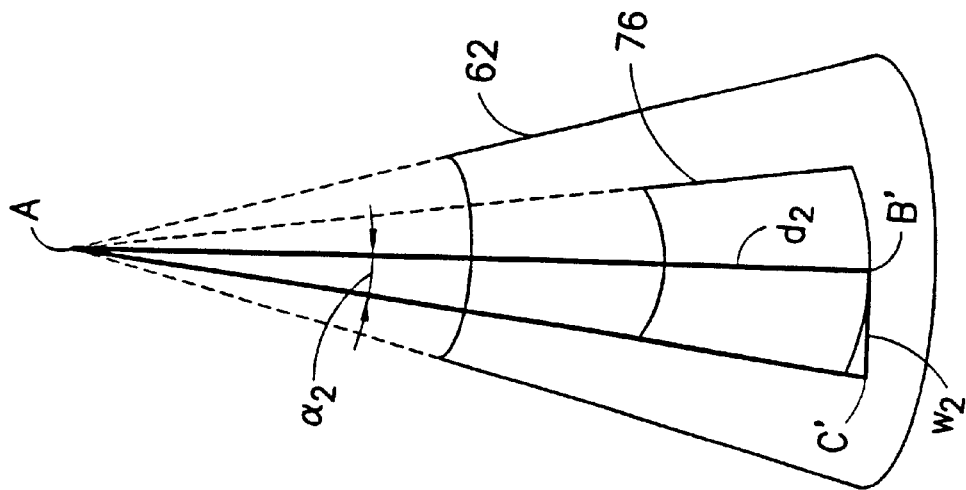
FIGS. 9 and 10 are schematics depicting the geometry used to calculate the respective half-widths of an ROI at initial (FIG. 9) and final (FIG. 10) positions in accordance with the algorithm of the preferred embodiment.
Figure 9:
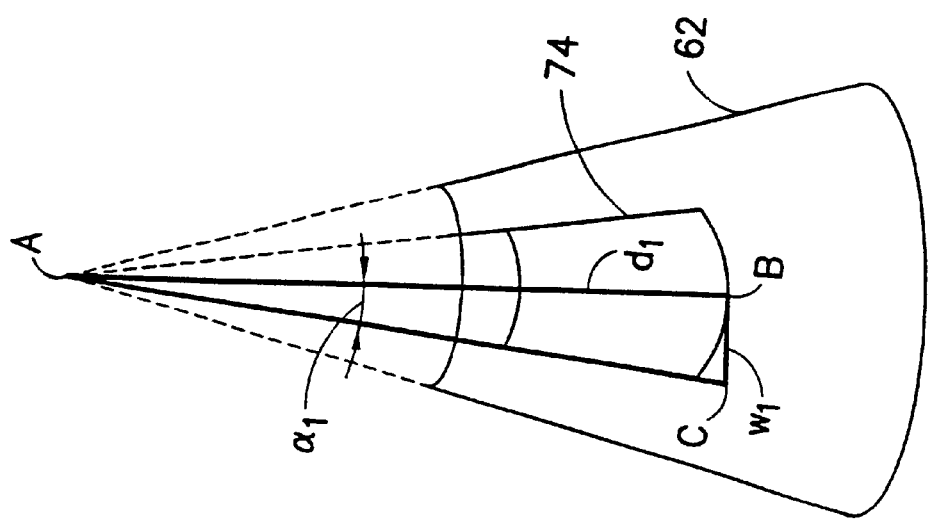

In accordance with the preferred embodiment of the invention, at the start of the algorithm the host computer has stored in its memory two parameters which define the initial location of the ROI. Referring to FIG. 9, the first parameter is the depth $d_1$, which is the distance from the image apex A to the center B of the bottom of ROI 74, and the second parameter is the angle $\alpha_1$, which is the angle between the line segment AB and a line segment AC collinear with the left edge of the ROI 74. The half-width $w_1$ of the ROI 74 (line BC in FIG. 9) can then be computed from $d_1$ and $\alpha_1$ as follows:

$$w_1 = d_1 \tan \alpha_1 \tag{9}$$

where the angle between line segments AB and BC is a right angle. In accordance with the preferred embodiment, when the user moves the ROI to the position shown in FIG. 10 without changing either the height or the bottom width of the ROI, the host computer first determines the new depth $d_2$, i.e., the movement directly dictates the distance from the image apex A to the center B' of the new ROI 76. The half-width $w_2$ (line segment B'C') of the new ROI 76 is set equal to the half-width $w_1$ of the old ROI 74, where the angle between line segments AB' and B'C' is again a right angle. With both $d_2$ and $w_2$ known, the host computer then calculates the new angle $\alpha_2$ between line segments AB' and AC' as $$\alpha_2 = \tan^{-1}(w_2/d_2) \tag{10}$$

This angle defines the orientation of the left edge of the ROI 76. The same computation can be performed for the other half of the ROI, thereby defining the orientation of the right edge of the ROI 76.

In accordance with the foregoing algorithm, the host computer is also programmed to calculate the pixel coordinates for the midpoint of the bottom arc of the ROI 76 (point B' in FIG. 10) as a function of the positioning of the ROI by the user. The height and the width of the ROI 76 are also already known, i.e., the height and width are the same as for the ROI 74 shown in FIG. 9. Computation of the angle between the left edge and the centerline (line segment AB') of the ROI 76, in combination with the ROI height and width and the pixel coordinates of the bottom midpoint, allows the host computer to compute the pixel coordinates of the left edge of the ROI 76. Similarly, the host computer computes the pixel coordinates of the right edge of the ROI 76. The pixel coordinates of the ROI bottom can be computed based in part on the pixel coordinates of B' and the radius $d_2$ (line segment AB'), while the pixel coordinates of the ROI top can be computed based in part on the pixel coordinates of B' and the radius ($d_2$-h), where h is the height of the ROI. The host computer outputs graphics data to addresses in the graphics display memory 41 corresponding to the set of pixel coordinates representing ROI 76. It should be appreciated that the computations of the ROI pixel coordinates are performed instantaneously in response to operator inputs changing the position of the ROI.

In accordance with another preferred embodiment, the first imaging mode is a non-optimal image quality B mode and the second imaging mode is an optimal image quality B mode. In this embodiment, the optimal image quality within the ROI is achieved by using a set of imaging parameters which are different than the set of imaging parameters used to acquire the image data in the background region. The different imaging parameters of the ROI as compared to the background region may include, e.g., different (e.g., shorter) transmit waveforms, an increased number of transmit focal zones per unit depth, different transmit and/or receive apertures, different center frequencies for the receive bandpass filter (primary and/or (sub)harmonics), and higher vector density (i.e., decreased vector spacing). Since the optimal imaging is restricted to an ROI, a high frame rate is still possible within the ROI depending on its size. The background image (outside the ROI) is to be maintained at or above some minimum acceptable level in terms of resolution and/or frame rate.

The ROI adjustment function is not limited to being implemented in an ultrasound imaging system, but instead can be implemented in any phased array imaging system which uses a curved linear or sector transducer array. In addition, the computations may be performed by a dedicated graphics processor instead of by the host computer. Also, the half-width need not be computed as the distance along the line segment connecting the midpoint of the bottom arc with a projection of an edge line. For example, the half-width could in the alternative be computed as half the distance along a line segment connecting the endpoints of the bottom arc. Regardless of which computation is used, the half-width is maintained constant in response to changes in ROI depth.

Figure 11:
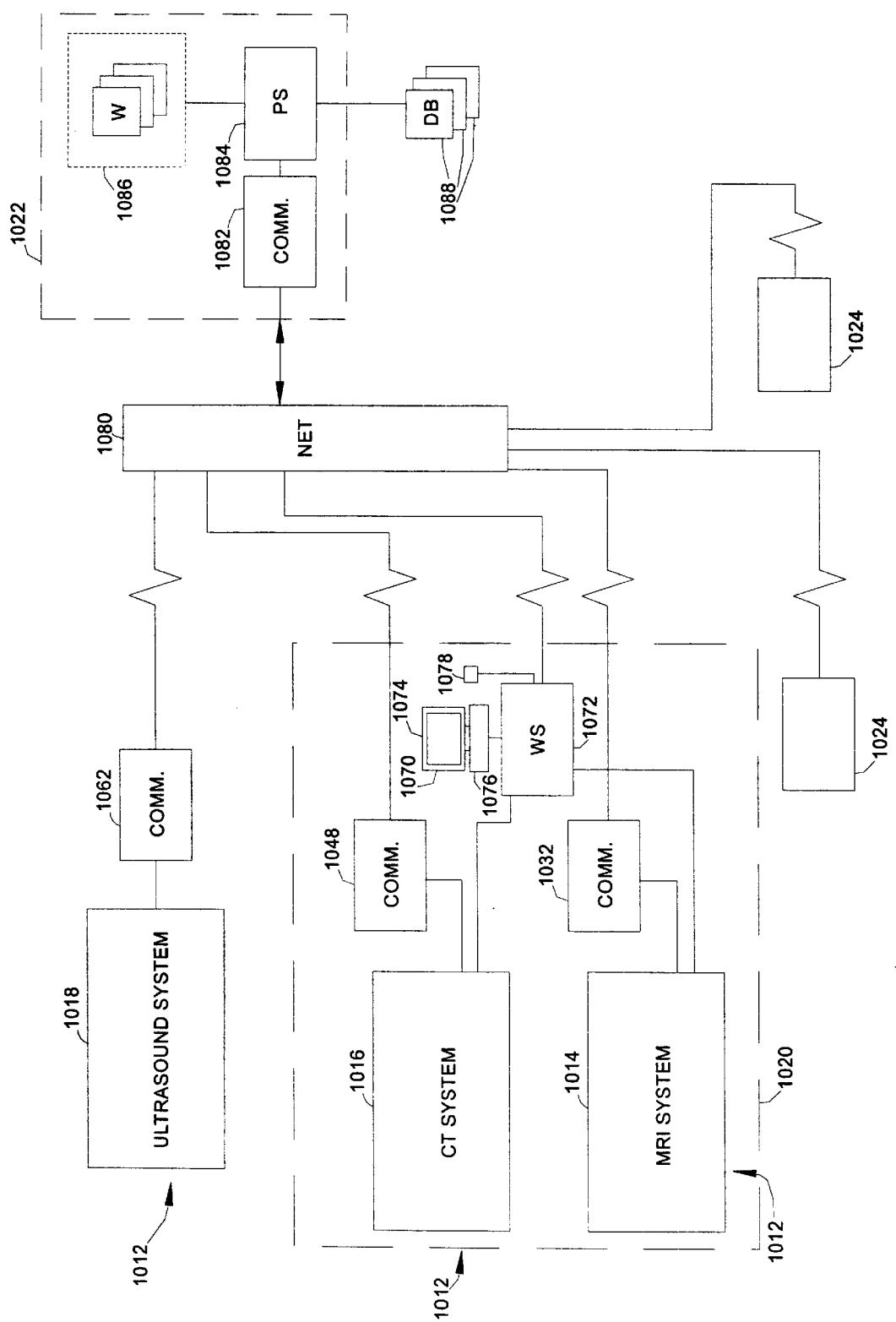
FIG. 11 is a diagrammatical representation of a series of medical diagnostic systems coupled to a service facility via a network connection for providing remote services and data interchange between the diagnostic systems and the service facility.

Referring now to FIG. 11, a service system 1010 is illustrated for providing remote service to a plurality of medical diagnostic systems 1012, including systems such as the ultrasound imaging system described with reference to FIG. 1. In the embodiment illustrated in FIG. 11, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 11, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 11, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 11. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 12:
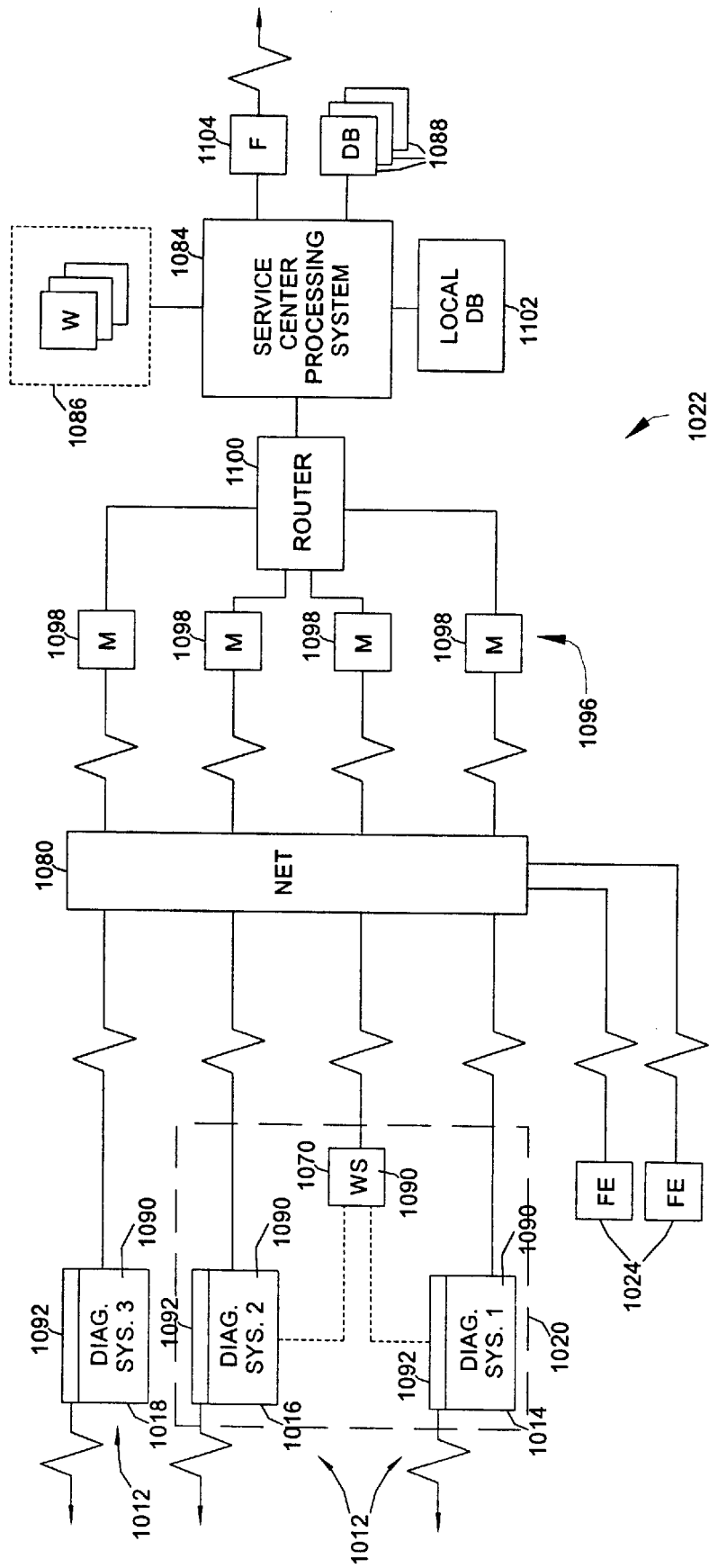
FIG. 12 is a block diagram of the systems shown in FIG. 11 illustrating certain functional components of the diagnostic systems and the service facility.

FIG. 12 is a block diagram illustrating the foregoing system components in a functional view. As shown in FIG. 12, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 13, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 12, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 13:
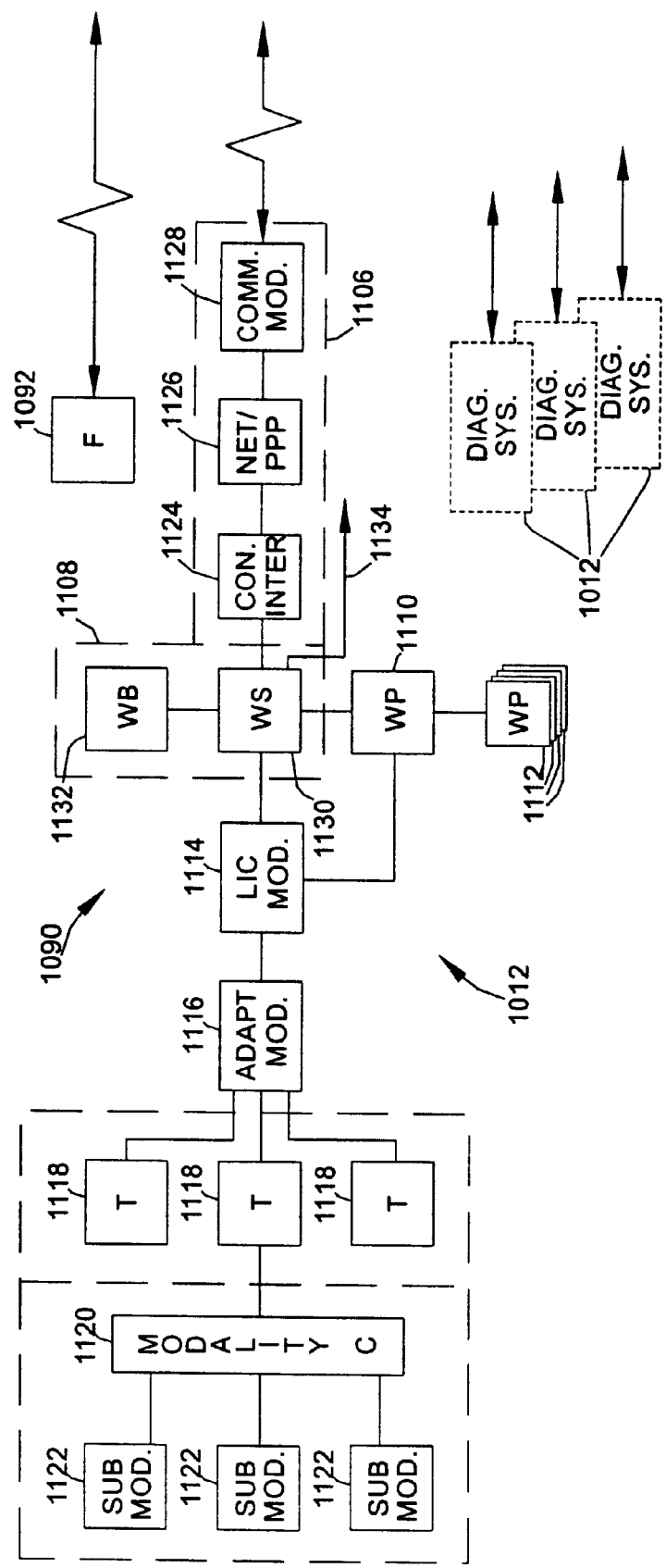
FIG. 13 is a block diagram of certain functional components within a diagnostic system of the type shown in FIG. 11 and FIG. 12 for facilitating interactive remote servicing of the diagnostic system.

FIG. 13 illustrates diagrammatically the various functional components comprising the uniform service platform 1090 within each diagnostic system 1012. As shown in FIG. 13, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 11 and 12).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 14:
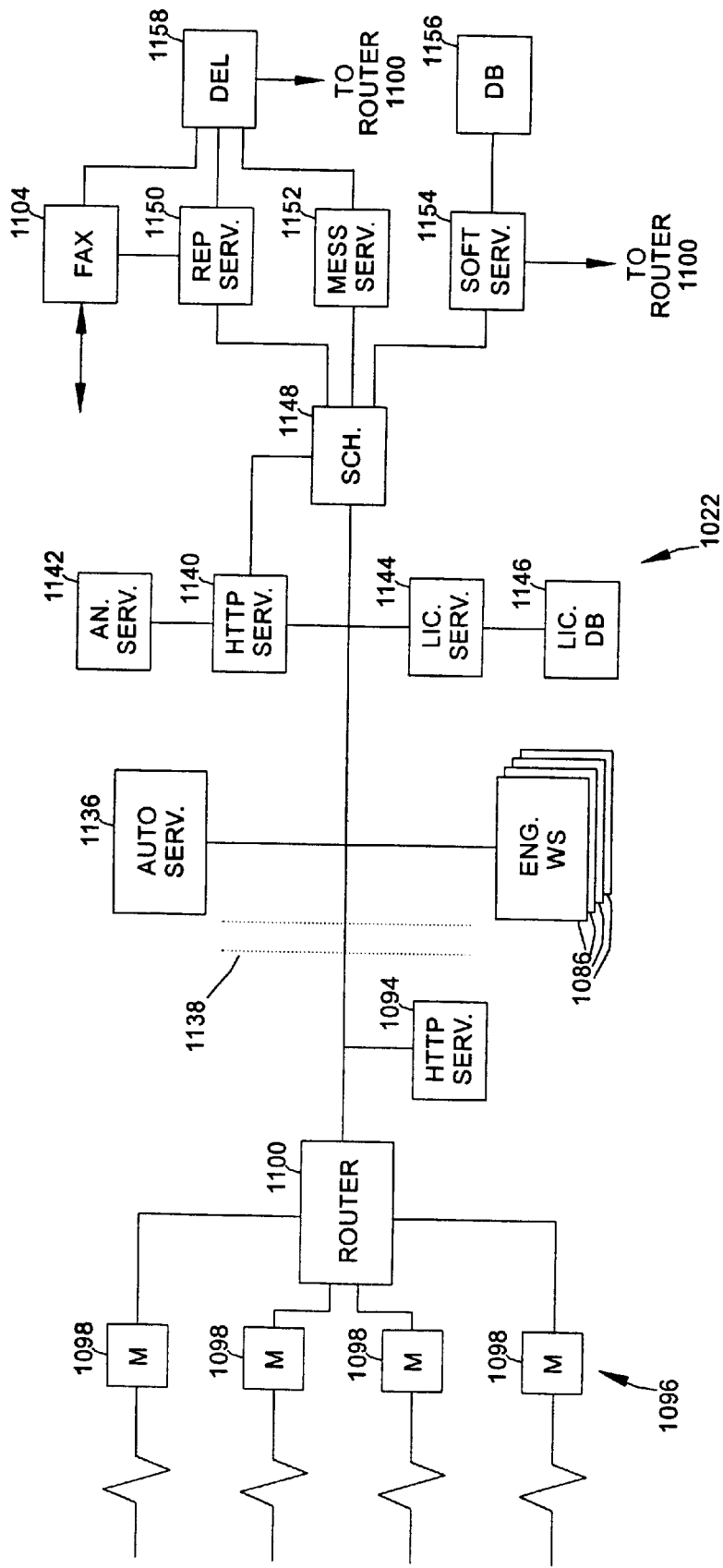
FIG. 14 is a block diagram of certain of the functional components of the service facility illustrated in FIG. 11 and FIG. 12 for rendering interactive remote service to a plurality of medical diagnostic systems.

FIG. 14 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 14, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 11) provides remote services, such as, software upgrades, remote operations control, remote diagnostics, and servicing. Positioning the region of interest and imaging of the region of interest may utilize and be enhanced by the functionalities of the service system 1010 as described herein.

While the embodiments illustrated in the Figures and described above are presently preferred, it should be understood that the embodiments are offered by way of example only. Other embodiments may include enhanced remote features made possible by the network structures and functionality described herein. The invention is not limited to a particular embodiment, but extends to various modifications, combinations, and permutations that nevertheless fall within the scope and spirit of the appended claims.

What is claimed is:

1. A method for displaying a region of interest graphic on an imaging system, comprising the steps of:
   a) establishing a communication connection over a network between the imaging system and a remote facility;
   b) displaying an image frame, the image frame having a reference point;
   c) displaying a region of interest graphic on the image frame at a depth determined relative to the reference point, the region of interest graphic having a bottom width, a top width, a height, and an angle between a projection of a first edge line and a projection of a second edge line;
   d) changing the depth of the region of interest; and
   e) changing the top width and the angle of the region of interest graphic as a function of the change in depth, while maintaining the height and the bottom width of the region of interest graphic substantially unchanged, wherein at least one of steps b) through e) is done remotely over the communication connection.

2. The method as recited in claim 1, wherein the step of establishing a communication connection over a network to provide remote services comprises at least one of upgrading the imaging system software, controlling operations of the imaging system remotely, diagnosing remotely, and servicing the imaging system remotely.

3. The method as recited in claim 1, wherein the top width is increased in response to an increase in depth and decreased in response to a decrease in depth.

4. The method as recited in claim 1, wherein the angle is increased in response to an increase in depth and decreased in response to a decrease in depth.

5. The method as recited in claim 1, wherein the region of interest graphic comprises first and second arcs connected at their respective ends by the first and second edge lines, the first and second arcs having a common center of curvature at the reference point, and the projections of the edge lines intersecting at the reference point.

6. The method as recited in claim 1, further comprising the steps of:
   acquiring imaging data in a first imaging mode for display on that portion of the image frame lying within the region of interest graphic; and
   acquiring imaging data in a second imaging mode for display on at least that portion of the image frame lying outside the region of interest graphic.

7. The method as recited in claim 6, wherein the acquiring step in the first imaging mode comprises the step of interrogating a first region of a scanning plane corresponding to the portion of the image frame lying outside the region of interest graphic with beams of wave energy, and the acquiring step in the second imaging mode comprises the step of interrogating a second region of the scanning plane corresponding to the region of interest with beams of wave energy.

8. The method as recited in claim 6, wherein each of the acquiring steps comprises the steps of transmitting beams of ultrasound energy into a body and detecting ultrasound energy returned from the body following each transmission.

9. The method as recited in claim 1, wherein the step of changing the depth of the region of interest graphic comprises the step of manipulating an input device on an operator interface.

10. The method as recited in claim 5, wherein the step of changing the top width and angle of the region of interest graphic comprises the steps of:
    determining a half-width of the bottom width; and
    determining an angle included between the first edge line and a midline connecting the reference point and a midpoint of the second arc as a function of the half-width and the depth.

11. An imaging method for an imaging system comprising the steps of:
    a) establishing a communication connection over a network between the imaging system and a remote facility;
    b) acquiring first imaging data in a first imaging mode from a first region in a scan plane;
    c) acquiring second imaging data in a second imaging mode from a second region in the scan plane;
    d) displaying the first imaging data in a region of interest of an image frame having a reference point, the region of interest being in the shape of a sector of an annular ring and placed at a depth determined relative to the reference point;
    e) displaying the second imaging data in a portion of the image frame lying outside the region of interest;
    f) changing the depth of the region of interest;
    g) adjusting the shape of the region of interest by changing a top width of the region of interest as a function of the change in depth while maintaining a height and a bottom width of the region of interest substantially constant;
    h) acquiring third imaging data in the first imaging mode from a third region in the scan plane;

i) acquiring fourth imaging data in the second imaging mode from a fourth region in the scan plane;

j) displaying the third imaging data in the adjusted region of interest; and k) displaying the fourth imaging data in a portion of the image frame lying outside the adjusted region of interest, wherein at least one of steps b) through k) is done remotely over the communication connection.

12. The method as recited in claim 11, wherein the step of establishing a communication connection over a network to provide remote services comprises at least one of upgrading the imaging system software, controlling operation of the imaging system remotely, diagnosing remotely, and servicing the imaging system remotely.

13. The method as recited in claim 11, wherein each of the acquiring steps comprises the steps of transmitting beams of ultrasound energy into a body and detecting ultrasound energy returned from the body following each transmission.

14. The method as recited in claim 11, further comprising the step of displaying a region of interest graphic superimposed on the image frame and bounding the adjusted region of interest.

15. The method as recited in claim 14, wherein the region of interest graphic comprises first and second arcs connected at their respective ends by the first and second edge lines, the first and second arcs having a common center of curvature at the reference point, and the projections of the edge lines intersecting at the reference point.

16. The method as recited in claim 11, wherein the top width is increased in response to an increase in depth and decreased in response to a decrease in depth.

17. An imaging system comprising:

a) means for establishing a communication connection over a network between the imaging system and a remote facility to provide remote services to the imaging system;

b) a display subsystem;

c) means for controlling the display subsystem to display an image frame, the image frame having a reference point;

d) means for controlling the display subsystem to display a region of interest graphic on the image frame at a depth determined relative to the reference point, the region of interest graphic having a bottom width, a top width, a height, and an angle between a projection of a first edge line and a projection of a second edge line;

e) means for changing the depth of the region of interest; and f) means for changing the top width and the angle of the region of interest graphic as a function of the change in depth, while maintaining the height and the bottom width of the region of interest graphic substantially unchanged.

18. The imaging system as recited in claim 17, wherein the remote services comprise at least one of imaging system software upgrades, remote control of imaging system operating systems, remote diagnostics, and remote servicing of the imaging system.

19. An imaging system comprising:

a) means for establishing a communication connection over a network between an imaging system and a remote facility to provide remote service to the imaging system;

b) a display subsystem;

c) means for acquiring first imaging data in a first imaging mode from a first region in a scan plane;

d) means for acquiring second imaging data in a second imaging mode from a second region in the scan plane;

e) means for controlling the display subsystem to display the first imaging data in a region of interest of an image frame having a reference point, the region of interest being in the shape of a sector of an annular ring and placed at a depth determined relative to the reference point;

f) means for controlling the display subsystem to display the second imaging data in a portion of the image frame lying outside the region of interest;

g) means for changing the depth of the region of interest;

h) means for adjusting the shape of the region of interest by changing a top width of the region of interest as a function of the change in depth, while maintaining a height and a bottom width of the region of interest substantially constant;

i) means for acquiring third imaging data in the first imaging mode from a third region in the scan plane;

j) means for acquiring fourth imaging data in the second imaging mode from a fourth region in the scan plane;

k) means for controlling the display subsystem to display the third imaging data in the adjusted region of interest; and l) means for controlling the display subsystem to display the fourth imaging data in a portion of the image frame lying outside the adjusted region of interest, wherein at least one of the means b) through l) is located remotely.

20. The imaging system as recited in claim 19, wherein the remote services comprise at least one of imaging system software upgrades, remote control of imaging system operating systems, remote diagnostics, and remote servicing of the imaging system.

21. The system as recited in claim 19, wherein the acquiring means comprise an ultrasound transducer array, a transmitter for activating the ultrasound transducer array to transmit beams of ultrasound energy into a body, and a receiver for detecting ultrasound energy returned to the ultrasound transducer array from the body following each transmission.

22. The system as recited in claim 19, further comprising means for controlling the display subsystem to display a region of interest graphic superimposed on the image frame and bounding the adjusted region of interest.

23. The system as recited in claim 19, wherein the region of interest graphic comprises first and second arcs connected at their respective ends by the first and second edge lines, the first and second arcs having a common center of curvature at the reference point, and the projections of the edge lines intersecting at the reference point.

24. The system as recited in claim 19, wherein the means for changing the depth of the region of interest comprise an operator-actuatable input device.

25. An imaging system comprising:

a display subsystem;

a network operatively coupled to the display subsystem and providing for the following steps, at least one of which is done remote from the display subsystem;

controlling the display subsystem to display an image frame, the image frame having a reference point;

controlling the display subsystem to display a region of interest graphic on the image frame at a depth determined relative to the reference point, the region of interest graphic having a bottom width, a top width, a height, and an angle between a projection of a first edge line and a projection of a second edge line;

changing the depth of the region of interest; and changing the top width and the angle of the region of interest graphic as a function of the change in depth while maintaining the height and the bottom width of the region of interest graphic substantially unchanged.

26. The system as recited in claim 25, further comprising an array of transducer elements, an array of pulsers respectively coupled to the transducer elements in a transmit mode, and an array of analog-to-digital converters respectively coupled to the transducer elements in a receive mode, wherein the network is operatively coupled to the pulsers and to the analog-to-digital converters and further provides for the following steps, at least one of which is done remotely from the display subsystem:

controlling the transducer elements of the array via the pulsers in a first imaging mode to interrogate a first region of a scan plane corresponding to a background portion of the image frame with beams of wave energy, the background portion lying outside the region of interest;

deriving first imaging mode data from digital data converted by the analog-to-digital converters from wave energy returned to the transducer elements of the array subsequent to each interrogation in the first imaging mode;

controlling the transducer elements of the array via the pulsers in a second imaging mode to interrogate a second region of the scan plane corresponding to the region of interest with beams of wave energy;

deriving second imaging mode data from digital data converted by the analog-to-digital converters from wave energy returned to the transducer elements of the array subsequent to each interrogation in the second imaging mode; and controlling the display subsystem to display the first imaging mode data in the background portion of the image frame and to display the second imaging mode data in the region of interest.

27. The system as recited in claim 25, wherein the network further provides for the step of controlling the display subsystem to display a region of interest graphic superimposed on the image frame and bounding the region of interest.

28. The system as recited in claim 27, wherein the region of interest graphic comprises first and second arcs connected at their respective ends by the first and second edge lines, the first and second arcs having a common center of curvature at the reference point, and the projections of the edge lines intersecting at the reference point.

29. The system as recited in claim 25, further comprising an operator-actuatable input device connected to the network, wherein the network provides the step of changing the depth of the region of interest in response to receipt of a predetermined command input via the input device.

30. The system as recited in claim 26, wherein each of the transducer elements transmits an ultra-sound wave in response to an electrical activation signal from a respective pulser and outputs an electrical receive signal to a respective analog-to-digital converter in response to receipt of an ultrasound wave.

* * * * *